United States Patent [19]

Savins

[11] 4,079,544
[45] Mar. 21, 1978

[54] OIL RECOVERY PROCESS EMPLOYING THICKENED AQUEOUS DRIVING FLUID

[75] Inventor: Joseph George Savins, Dallas, Tex.

[73] Assignee: Mobil Oil Corporation, New York, N.Y.

[21] Appl. No.: 680,819

[22] Filed: Apr. 28, 1976

[51] Int. Cl.² .......................... A01G 7/00; C09K 3/00
[52] U.S. Cl. ................................. 47/1.4; 252/8.55 R
[58] Field of Search ................... 252/8.55; 47/1.4, 58

[56] References Cited

U.S. PATENT DOCUMENTS

| 2,731,414 | 1/1956 | Binder et al. | 252/8.55 |
| 3,879,890 | 4/1975 | Chen et al. | 47/1.4 |
| 3,889,418 | 6/1975 | Porter et al. | 47/58 |
| 3,958,364 | 5/1976 | Schenck et al. | 47/1.4 |
| 3,969,844 | 7/1976 | Fogel et al. | 47/58 |

OTHER PUBLICATIONS

The Production of ———, Ramus, Jul. Phycol. 8, 1972, pp. 97–111.

*Primary Examiner*—Robert E. Bagwill
*Attorney, Agent, or Firm*—C. A. Huggett; William D. Jackson

[57] ABSTRACT

This specification discloses a process for the production of petroleum from a petroleum-containing subterranean reservoir employing an aqueous driving fluid containing, as a thickening agent, a biopolymer. The biopolymer is an extracellular heteropolysaccharide synthesized by an alga. A particular bipolymer is one synthesized by the alga *Porphyridium aerugineum*. The biopolymer may be employed in the aqueous driving fluid as an in-vivo solution or in a reconstituted form. There is also disclosed a process for the growth of, and synthesis of, biopolymer by an alga such as *Porphyridium aerugineum*.

29 Claims, 8 Drawing Figures

OIL RECOVERY PROCESS EMPLOYING THICKENED AQUEOUS DRIVING FLUID

BACKGROUND OF THE INVENTION

1. Field of the Invention

This invention relates to the production of petroleum from a petroleum-containing subterranean formation employing an aqueous driving fluid containing, as a thickening agent, a biopolymer synthesized by an alga and to the synthesis of the biopolymer by an alga such as *Porphyridium aerugineum*.

2. Description of the Prior Art

Processes for the production of petroleum from a petroleum-containing subterranean formation employing an aqueous driving fluid containing a thickening agent is well known. U.S. Pat. No. 3,020,207 discloses such a process where the thickening agent is a heteropolysaccharide that has been reacted with an aldehyde, the heteropolysaccharide being a fermentation product produced by the action of bacteria of the genus *Xanthomonas* upon a carbohydrate. U.S. Pat. No. 3,352,358 discloses a process employing thickened aqueous driving fluid where the thickening agent is polyvinyl alcohol sulfate. U.S. Pat. No. 3,372,749 also discloses a process employing thickened aqueous driving fluid where the thickening agent is a poly(glucosylglucan). In the process disclosed in U.S. Pat. No. 3,373,810, the thickening agent for the aqueous driving fluid is sulfoalkylated poly(glucosylglucan), a sulfoalkylated polysaccharide or a mixture of both, the polysaccharide being the heteropolysaccharide produced by the action of the bacterium *Xanthomonas campestris* on glucose.

Procedures for the growth of algae are also well known. For example, U.S. Pat. No. 3,195,271 discloses a process for the growth of the alga *Porphyridium cruentum*. This patent also discloses the synthesis of the alga constituent, carrageenin, and discloses that the liquid phase of the culture in which the alga is grown is viscous or mucilaginous. Procedures for the growth of alga are also disclosed in "Algal Culture: From Laboratory to Pilot Plant", J. S. Burlew, Ed., Carnegie Inst. of Washington, Publication No. 600, Washington, D. C. (1964), and "Properties and Products of Algae", J. S. Zajic, Ed., Plenum Press, N. Y. (1970). It is also well known that many marine and fresh water species of alga liberate synthesis products into their surroundings that have drag reducing properties, Hoyt, J. W., and Soli, G., Science, 149, 1509 (1965). The influence of light quality on the production of algal biomass production is disclosed in "Spectral Light Requirements of Algae", Brown, T. E., Tech. Report No. 69-45-FL, U.S. Army Natick Labs., October, 1968.

SUMMARY OF THE INVENTION

The invention is directed to the production of petroleum from a petroleum-containing subterranean formation. An aqueous driving fluid is injected into the formation through an input well and passed through the formation in the direction of an output well to drive the petroleum in the formation to the output well. The aqueous driving fluid contains a thickening agent and the thickening agent is a biopolymer, a heteropolysaccharide synthesized by an alga.

The invention is also directed to the synthesis of the biopolymer by an alga such as *Porphyridium aerugineum*. The culture for the synthesis of the biopolymer contains in addition to the usual microelements required for growth of the alga sodium nitrate in the amount of about 60 to 250 weight parts per million (wppm) and sodium glycerophosphate in the amount of about 100 to 300 weight parts per million. The synthesis of the biopolymer may also be carried out under such conditions of illumination of the culture that three radiant energy-related parameters are controlled, namely: (a) the intrinsic slope of the initial segment of the cumulative absorbed radiant energy versus time curve, denoted $\psi_a$; (b) the cumulative moles of light quanta absorbed, denoted $(E_a)_c$; and (c) the group formed by the ratio of (a) to (b), denoted $\Delta$. In a specific embodiment of the synthesis of biopolymer by *Porphyridium aerugineum*, $\psi_a$ is about 0.33 Einstein (0.0165 kw-hr) per liter of culture per day, $(E_a)_c$ is between about 1.2 to 2.0 Einsteins (0.06 to 0.10 kw-hr) per liter of culture and the value of $\Delta$ is about 0.18 per day. The synthesis of the biopolymer may also be carried out by a two-stage process. In this process, the three aforementioned radiant energy-related parameters are manipulated. In the first stage, the culture is subjected to artificial illumination and is continued for a period of time that growth of the alga and synthesis of the biopolymer begin. In the second stage, the culture is subjected to diurnal natural illumination to continue alga growth and synthesis of the biopolymer. The growth of the alga and synthesis of the biopolymer may also be carried out employing an illumination regime wherein the energy content of the illumination is enriched with respect to particular wavelengths. In the synthesis of biopolymer by *Porphyridium aerugineum*, the energy content of the illumination is predominantly in the region of 600 to 700 nanometers. The biopolymer may also be upgraded with respect to its thickening characteristics by complexing with a heavy metal or transitional metal ion such as trivalent chromium ion. Biopolymer may also be synthesized by an alga at the site where the aqueous driving fluid containing the biopolymer as thickening agent is injected into the subterranean reservoir.

DESCRIPTION OF THE PREFERRED EMBODIMENTS

Figure 1:
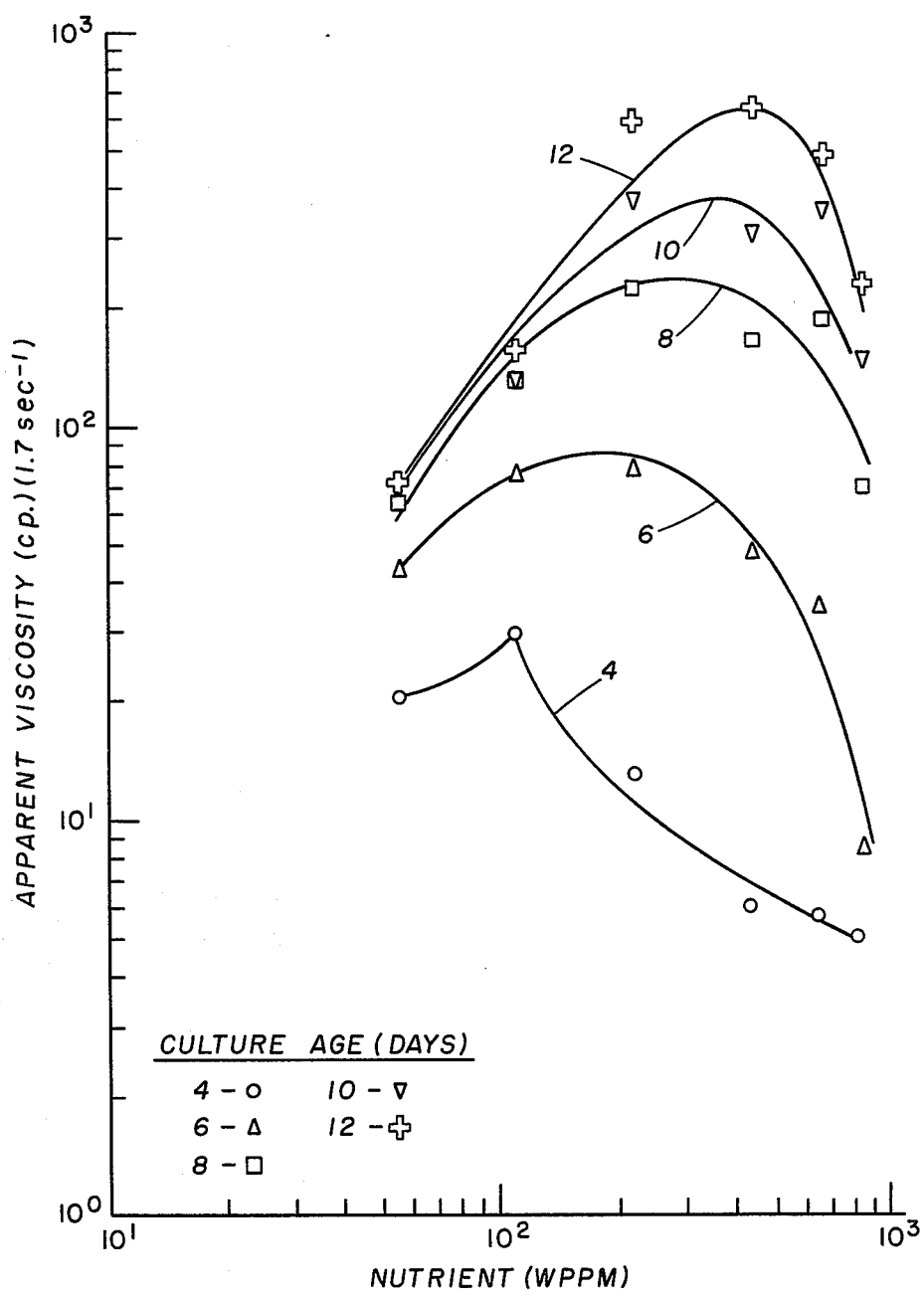
FIG. 1 is a plot of attained apparent viscosity of a culture versus sodium nitrate concentration in the culture.

Liquid petroleum accumulated within a subterranean formation can be produced, or recovered, therefrom through wells leading from the surface of the earth to the formation using the natural energy within the formation. However, the natural energy in the formation is insufficient to recover all of the petroleum and becomes rapidly depleted. Thus, a large amount of the petroleum is left in a subterranean formation if only the natural energy is used to produce the petroleum. This production by depletion of the natural energy is often referred to as primary production. Where natural energy has become depleted, supplemental operations, often referred to as secondary recovery operations, or tertiary if there is more than one such supplemental operation, are used to improve the extent of recovery of the petroleum. In the most successful and most widely used supplemental recovery operation, a fluid is injected through an injection means comprising one or more input wells. The fluid enters the formation and passes through the formation in the direction of a production means comprising one or more output wells. The fluid displaces the petroleum within the formation and the petroleum passes through the formation along with the fluid in the direction of the output means. The petroleum is produced from the production means. In a particular supplemental recovery operation of this sort, an aqueous driving fluid is employed and the operation is referred to as waterflooding.

While waterflooding is effective in obtaining additional petroleum from a petroleum-containing subterranean formation, it has a number of shortcomings. Foremost among these shortcomings is the tendency of the aqueous driving fluid to "finger" through the petroleum-containing formation and thus bypass substantial portions of the formation. By "fingering" is meant the development of unstable bulges or stringers which advance toward the production means more rapidly than the remainder of the aqueous driving fluid.

It has been established that waterfloods perform less satisfactorily with viscous petroleum than with relatively nonviscous petroleum. The fingering tendencies of the aqueous driving fluid are more or less directly related to the ratio of the viscosity of the petroleum to the viscosity of the aqueous driving fluid. The viscosities of different petroleums vary from as low as 1 or 2 centipoises (0.001 to 0.002 pascal-second) to 1000 centipoises (1 pascal-second) or higher whereas water has a viscosity of about 1 centipoise (.001 pascal-second).

The relationship between the mobility of the petroleum and of the aqueous driving fluid in a particular formation is related to their respective viscosities according to the following equation:

$$\frac{M_p}{M_a} = \left(\frac{\mu_a}{\mu_p}\right)\left(\frac{K_p}{K_a}\right)$$

where
$M_p$ is the mobility of the petroleum in the formation,
$M_a$ is the mobility of the aqueous driving fluid in the formation,
$\mu_p$ is the viscosity of the petroleum,
$\mu_a$ is the viscosity of the aqueous driving fluid,
$K_a$ is the relative permeability of the formation to the aqueous driving fluid in the presence of the petroleum which remains in the formation after passage of the aqueous driving fluid, and
$K_p$ is the relative permeability of the formation to the petroleum in the presence of the connate water in the formation.

In a subterranean formation containing petroleum having a high viscosity, in order to achieve a mobility ratio of 1, i.e., where the aqueous driving fluid and the petroleum move through the formation with equal facility and fingering is thus minimized, the viscosity of the aqueous driving fluid must be increased. In the absence of severe differences in the relative permeabilities of the petroleum and of the aqueous driving fluid, the mobilities of the petroleum and the aqueous driving fluid are inversely proportional to the viscosities of the petroleum and the aqueous driving fluid.

Past suggestions for increasing the viscosity of the aqueous driving fluid have included incorporating water-soluble thickening agents in the aqueous driving fluid.

In accordance with one aspect of the present invention, the aqueous driving fluid injected into the petroleum-containing subterranean formation contains as a thickening agent a biopolymer synthesized by an alga.

Many algae, during their life cycle in a culture, synthesize extracellular biopolymers, and these extracellular biopolymers enter into the culture. These biopolymers may be of a viscous nature, thus imparting thickening to an aqueous medium containing them. Provided they impart satisfactory thickening to an aqueous driving fluid in the presence of brines and divalent ions contained in a petroleum-containing subterranean formation, do not preferentially absorb out of the fluid onto formation solids, and are stable in a petroleum-containing subterranean formation, they may be employed in the recovery of petroleum from a subterranean petroleum-containing formation.

The biopolymers synthesized by various algae may be employed in the practice of the invention for recovery of petroleum. Satisfactory polysaccharides for use in the process of the invention are synthesized by algae from the divisions Chlorophyta, Phaeophyta, Rhodophyta, and Cyanophyta. In the division Chlorophyta, those synthesized by the genus Ulva may be employed. In the division Phaeophyta, those from the genera Ilea and Pelvetiopsis may be employed. In the division Rhodophyta, those from the genera Porphyra, Corallina, Gratelupia, Gymnogongrus, Stenogramma, and Rhodomenia may be employed. In the division Cyanophyta, those from the genus Anabaena may be employed. In the genus Porphyra, those from the species *Porphyridium aerugineum* and *Porphyridium cruentum* may be employed. In the genus Anabaena, those from the species *Anabaena flos-aquae* may be employed. In the division Chlorophyta, those from the species Chlorella stigmataphora may be employed. Preferably, the polysaccharides synthesized by the species *Porphyridium aerugineum* are employed.

Synthesis of the biopolymers as thickening agents for the aqueous driving fluid is obtained by growth of the alga in a culture. Required in the culture for growth of the algae and synthesis of the biopolymer are, as is known, water and mineral salts. Also required is a source of carbon as a nutrient.

With growth of the alga and concomitant synthesis of the biopolymer, the viscosity of the culture increases as the concentration of the biopolymer increases. Growth of the alga and synthesis of the biopolymer may be continued until a desired viscosity level is achieved or until the ultimate maximum viscosity level is achieved. With termination of the growth of the alga and synthesis of the biopolymer, the alga biomass is separated, as by centrifugation, from the remainder of the culture. The remainder of the culture, i.e., the supernatant thickened aqueous solution of the biopolymer containing the mineral salts and any partially spent nutrient, is herein termed the in-vivo solution of the biopolymer. The in-vivo solution of the biopolymer may be employed as the thickening agent in the recovery of the petroleum from the subterranean petroleum-containing formation. On the other hand, the biopolymer may be separated from the supernatant in-vivo solution and the separated biopolymer employed as the thickening agent. The biopolymer may be recovered from the supernatant solution in such a way that it is presented as a slurry comprised of dispersed particles suspended in a nonaqueous carrier liquid which can be subsequently reconstituted. Typically, however, the separated biopolymer is reduced to a dried powder which can be reconstituted by addition of water and the reconstituted form employed as the thickening agent. Reconstitution may be effected simply by addition of the biopolymer to the aqueous driving fluid. Usually, as pointed out hereinafter in greater detail, the viscosity yield of the in-vivo form is greater than that of the reconstituted form and hence is a preferred form. The separated alga may be employed as inoculum in another cycle for synthesis of biopolymer.

Separation of the biopolymer from the in-vivo solution may be effected by any known means. For example, separation may be effected by addition to the solution of an alcohol or a quaternary ammonium compound such as cetyl pyridinium chloride. Preferably, isopropyl alcohol is employed. Addition of the alcohol or quaternary ammonium compound effects precipitation of the biopolymer. The precipitated biopolymer is then separated from the supernatant liquid.

The amount of biopolymer to be employed as thickening agent in the aqueous driving fluid will depend upon the desired viscosity of the aqueous driving fluid, i.e., the degree of mobility control desired. In some instances, the viscosity of the in-vivo solution will be equal to the desired viscosity of the aqueous driving fluid. In this case, the in-vivo solution, after conditioning as mentioned hereinafter, may be employed as the aqueous driving fluid. Where the viscosity of the in-vivo solution is greater than that required for mobility control, it may be diluted with make-up water and, after conditioning, employed as the aqueous driving fluid. Where the biopolymer is employed in the aqueous driving fluid in reconstituted form, the amount employed will again depend upon the degree of mobility control desired.

The following example will be illustrative of the effect of employing an aqueous driving fluid containing as a thickening agent a biopolymer synthesized by an alga.

EXAMPLE 1

In this example, petroleum was displaced from unconsolidated sand packs containing petroleum, i.e., crude oil, using aqueous driving fluid containing a thickening agent. The unconsolidated sand packs were constituted of Berea solids and had a permeability of 4 darcies (4 micrometers$^2$). The petroleum contained in the packs was Charamousca crude oil. In one instance, the thickening agent was an in-vivo solution of biopolymer synthesized by *Porphyridium aerugineum*. The latter is a fresh water species of a unicellular red alga. In another instance, the thickening agent was an in-vivo solution of biopolymer synthesized by *Porphyridium sp.*, a marine species of a unicellular red alga. In still another instance, for comparison purposes, the thickening agent was polysaccharide B-1459, a biopolymer produced by the action of the bacterium *Xanthomonas campestris* on glucose. The latter is a commercial thickening agent for use in aqueous driving fluids for the recovery of petroleum from subterranean formations and is sold under the trade name "Kelzan". The aqueous driving fluids were employed with and without added sodium hydroxide and contained varying amounts of sodium chloride as a salinity control agent. Where added sodium hydroxide was employed, the petroleum displacing procedure simulated an alkaline waterflooding operation. With the sand packs at the initial petroleum saturation, various aqueous driving fluids were passed in equal amount through the sand packs and the amount of the petroleum removed from the sand packs was measured. The conditions and the results are given in the following table. In the table, "N" refers to the normality of the sodium hydroxide solution, "$\eta$, cp." refers to the viscosity of the aqueous driving fluid in centipoises (1 centipoise is equal to 0.001 pascal-second), and "Residual Petroleum" refers to the percentage of the original petroleum remaining in the sand packs following passage therethrough of the aqueous driving fluid.

TABLE I

| Thickening Agent | NaOH, N | NaCl, % | C, WPPM | $\eta$, cp. | pH | Residual Petroleum, % |
|---|---|---|---|---|---|---|
| Biopolymer from |  | 1.5 | 1100 | 234 |  | 23.7 |
| *Porphyridium aerugineum* | 0.015 | 1.5 | 1100 | 232 | 12.24 | 5.64 |
| Biopolymer from | 0 | 1.0 | 1100 | 200 |  | 21.7 |
| *Porphyridium sp.* | 0.015 | 1.0 | 1100 | 200 | 12.23 | 15.6 |
|  | 0.015 | 1.25 | 1100 | 188 | 12.22 | 7.52 |
|  | 0.015 | 2.0 | 1100 | 196 | 12.24 | 6.36 |
|  | 0.015 | 2.5 | 1100 | 190 | 12.21 | 11.79 |
| Kelzan | 0 | 1.0 | 1500 | 300 |  | 19.2 |
|  | 0.015 | 1.25 | 1500 | 165 | 12.16 | 6.53 |
|  | 0.015 | 1.0 | 1500 | ~165 | ~12.16 | 9.7 |
|  | 0.015 | 2.0 | 1500 | ~165 | ~12.16 | 13.5 |

It will be observed from the table that the aqueous driving fluids containing the in-vivo suspensions of the biopolymers synthesized by the algae were, in terms of recovery of petroleum, equal to or superior to the aqueous driving fluid containing the Kelzan even though the concentration of the Kelzan was greater than that of the biopolymers synthesized by the algae.

In accordance with another aspect of the invention, there is provided a process for the synthesis of biopolymer by an alga such as *Porphyridium aerugineum*.

An alga such as *Porphyridium aerugineum* requires for its growth, illumination, a source of carbon, and certain other nutrients and nutrient-related constituents. With an alga which is an obligate photoautotroph, such as *Porphyridium aerugineum*, it is customary to provide the source of carbon in the form of gaseous carbon dioxide. Carbon dioxide also serves to act as a pH buffering agent in the culture. A standard culture for the growth of an alga such as *Porphyridium aerugineum*, known as the MCYII or "Ramus" medium, (Ramus, J., Jnl. Phycol., 8 [1], 97 (1972); and Gantt. E. et al., Jnl. Phycol., 4, 65 (1968)), contains the following distribution of macro and micro levels of inorganic ions, chelating agents, vitamins, etc.

TABLE II

| MCYII MEDIUM | | |
|---|---|---|
| $NaNO_3$ | 442 | mg |
| KCl | 30 | mg |
| $CaCl_2 \cdot 2H_2O$ | 36.6 | mg |
| $FeCl_3 \cdot 6H_2O$ | 1.9 | mg |
| $MgSO_4 \cdot 7H_2O$ | 100 | mg |
| $Na_2 \cdot$ glycerophosphate $\cdot 5H_2O$ | 90 | mg |
| Tricine buffer | 986 | mg |
| PII trace metal mix | 10 | ml |
| Vitamin $B_{12}$ | 3.5 | $\mu$g |
| Distilled water to | 1000 | ml |
| Adjust pH to 7.6 with NaOH | | |
| PII Metal Mix: | | |
| $H_3BO_3$ | 114.0 | mg |
| $MnCl_2 \cdot 4H_2O$ | 14.4 | mg |
| $ZnSO_4$ | 2.2 | mg |
| $CoCl_2 \cdot 6H_2O$ | 0.44 | mg |
| $FeCl_3 \cdot 6H_2O$ | 4.8 | mg |
| $Na_2EDTA$ | 100 | mg |
| Distilled water to | 100 | ml |

In this aspect of the invention, an alga such as *Porphyridium aerugineum* is grown and the biopolymer synthesized in a culture containing sodium nitrate in the amount of about 55 to 250 weights parts per million and sodium glycerophosphate in the amount of about 100 to 300 weight parts per million. Synthesis of the biopolymer in a culture containing these concentrations of sodium nitrate and sodium glycerophosphate results in a higher rate of formation of biopolymer, indicated by a higher rate of viscosity increase of the culture, as compared to the rate of formation of biopolymer synthesized in a culture containing sodium nitrate and sodium glycerophosphate in the conventional amounts as set forth in Table II above.

The following example will illustrate the kinetics of viscosity production and ultimate yields of biopolymer synthesized by *Porphyridium aerugineum* by the process of this aspect of the invention.

EXAMPLE 2

In this example, *Porphyridium aerugineum* was grown and biopolymer synthesized in a series of cultures having the composition set forth in Table II above. The particular *Porphyridium aerugineum* that was employed is cataloged as isolate No. 755 in the alga culture collection maintained at Indiana State University, Bloomington, Indiana, e.g., see Starr. R. C., Amer. Jnl. Bot., 51 [9], 1013 (1964). The same isolate was also employed in the other examples herein where the alga was *Porphyridium aerugineum*. The amounts of each of the sodium nitrate and the amounts of the sodium glycerophosphate were varied individually whereas the amounts of the other constituents were as indicated in Table II above. In carrying out the operations, the cultures were each inoculated with an inoculum taken from a culture in the log phase of growth. The amount of inoculum was such that the initial cell concentration was on the order of one to two million cells of the alga per milliliter of culture. The alga was grown, and the biopolymer synthesized, at 74° F. (23.3° C.) with an illumination level (incident light only) in the range from 600 – 1000 foot candles (6045.84 – 10076.4 lux). Agitation was provided by means of the conventional shake flask system. The carbon source was 5% carbon dioxide entrained with 95% air. Growth proceeded over a 12-day period. Samples of the culture were removed at 4, 6, 8, 10, and 12-day intervals and their apparent viscosity at a shear rate of 1.7 sec$^{-1}$ was measured employing a Brookfield viscometer fitted with a U.L. adapter. The apparent viscosity of the culture, as indicated above, is a measure of the concentration of the biopolymer in the culture. The results are given in FIGS. 1 and 2.

It will be observed from FIG. 1 that, with concentrations of sodium nitrate between about 56 to 220 weight parts per million, the apparent viscosities of the culture at the end of 4 days and 6 days were higher than those of the culture with the conventional 440 weight parts per million of the sodium nitrate. Thus, with concentrations of sodium nitrate of about 56 to 220 weight parts per million for the period between the beginning of synthesis of the biopolymer and 8 days of growth, the synthesis of the biopolymer is at a greater rate than with the conventional concentration of 440 weight parts per million.

Figure 2:
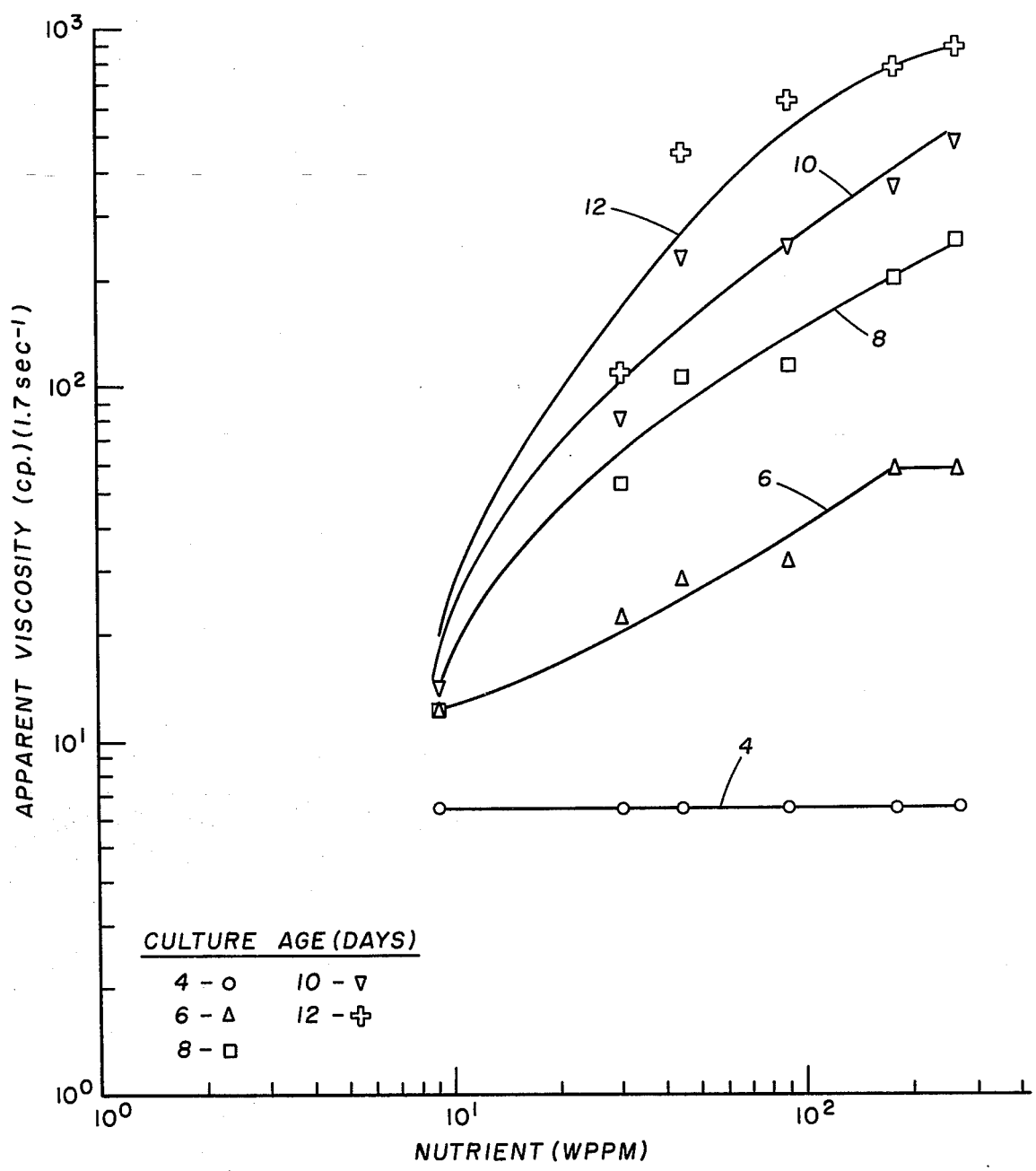
FIG. 2 is a plot of attained apparent viscosity of a culture versus sodium glycerophosphate concentration in the culture.

It will be observed from FIG. 2 that, up to 4 days of growth of the alga and synthesis of the biopolymer, the concentration of the sodium glycerophosphate had no effect on the apparent viscosity of the culture and thus on the rate of synthesis of the biopolymer. On the other hand, after 4 days, the apparent viscosities of the culture at concentrations of the sodium glycerophosphate in excess of about 90 weight parts per million were greater than the apparent viscosity of the culture having the conventional concentration of the sodium glycerophosphate of 90 weight parts per million indicating the more rapid rate of synthesis of the biopolymer.

In another aspect of the process, the synthesis of the biopolymer by the alga is carried out in a single-stage process. In this single-stage process, conditions of illumination with respect to light intensity and photoperiod are controlled. Three radiant energy-related parameters are controlled. The first parameter, ($a$), is the intrinsic slope of the initial segment of the cumulative absorbed radiant energy versus time curve, denoted ($\psi_a$). The second parameter, ($b$), is the cumulative moles of light quanta absorbed, denoted $(E_a)_c$. The third parameter, ($c$), is a group formed by the ratio of ($a$) to ($b$), denoted ($\Delta$).

For the synthesis of biopolymer from *Porphyridium aerugineum*, optimum management of biomass and bipolymer production results when $\psi_a$ is about 0.33 Einstein (0.0165 kw-hr) per liter of culture per day, $(E_a)_c$ is between about 1.2 to 2.0 Einsteins (0.060 to 0.100 kw-hr) per liter of culture, and $\Delta$ is about 0.18 per day. During the induction period, the value of $(E_a)_c$ is between about 0.66 to 0.89 Einstein (0.033 to 0.045 kw-hr) per liter of culture. The value of $\psi_a$ of about 0.33 Einstein per liter of culture per day (0.0165 kw-hr) corresponds to a minimum lag time ($\theta_l$) of about 40 hours. "Lag time" is herein defined as the induction period wherein radiant energy is being absorbed by the culture before growth of the alga and synthesis of the biopolymer begins.

The following example will be illustrative of the kinetics of the single-stage process for synthesis of the biopolymer.

EXAMPLE 3

In this example, *Porphyridium aerugineum* was grown and biopolymer synthesized in one-liter batches of culture. The cultures contained, in aqueous solution, the components set forth in Table III. The composition of this culture, with respect to the components thereof set forth in Table III, is disclosed and claimed in the copending application of Joseph George Savins and James M. Paul, Ser. No. 680,820, filed concurrently herewith and identified as Mobil Case No. 9063. The reactor for the growth of the alga and synthesis of the biopolymer consisted of two parallel polished sheets of lucite maintained 0.3 centimeter apart by spacers. Illumination (radiant energy) incident to and transmitted through the culture containing the alga was measured, the difference between the two being the illumination absorbed. During the synthesis, the incident illumination was held constant at an average value of the order of 10,593 ergs (1059.3 microjoules) cm$^{-2}$ sec$^{-1}$ and was provided by "Vitalite" fluorescent tubes. Details concerning the "Vitalite" tubes are set forth by Thorington, L., et al., IES Trans. and Jnl. of IES, pp. 33–41, October 1971. The growth of the alga and synthesis of the biopolymer was carried out for a period of 5 days, during which time a mixture of 5% carbon dioxide and 95% air was continuously injected into the reactor at a rate of 500 cc min$^{-1}$ liter$^{-1}$. The temperature was maintained at 76° ± 0.5° F. (24.4° ± 0.28° C.)

During the five-day period, the cumulative incident illumination was 4.43 Einsteins (.2215 kw-hr) and the cumulative absorbed illumination was 2.47 Einsteins (0.1335 kw-hr). During the first two days, $\psi_a$ was 0.885. The group $\psi_a/(E_a)_c$, i.e. ($\Delta$), accordingly was 0.182 per day. Synthesis of biopolymer began within 42 hours, i.e., the lag time, $\theta_b$, was 42 hours. The yield of biopolymer was 2.67 grams per liter corresponding to a low shear rate apparent viscosity of 1420 centipoises (1.420 pascal-seconds) of the culture. The yield of alga was of the order of 0.66 gram per liter. The efficiency of conversion of cumulative absorbed radiation to biopolymer was of the order of 11%. Efficiency of conversion of radiation to biopolymer is expressed as $$100 \left[ \frac{\text{chemical energy of biopolymer formed}}{\text{photochemical equivalents absorbed}} \right].$$

TABLE III

| Component | Concentration - WPPM |
|---|---|
| $MgSO_4 \cdot 7H_2O$ | 100 |
| $NaNO_3$ | 442 |
| $CaCl_2$ | 28 |
| $FeCl_3$ | 1.43 |
| *$K_2HPO_4$ | 51 |
| $H_3BO_3$ | 11.4 |
| $FeSO_4 \cdot 7H_2O$ | 2.2 |
| $ZnSO_4 \cdot 7H_2O$ | 1.44 |
| KCl | 30 |
| $B_{12}$ | $3.5 \times 10^{-6}$ |
| $CoCl_2 \cdot 6H_2O$ | 0.044 |
| $(Na)_2EDTA$ | 10 |
| Tricine Buffer | |

*Note:
42 wppm $Na_2HPO_4$ can be substituted as $PO_4^-$ source.

In another aspect of the process, growth of alga and synthesis of biopolymer is carried out in two stages. In the first stage, the culture containing the alga is subjected continuously to artificial illumination. In this process, the three radiant-energy parameters as described in connection with the single-stage process above are controlled. The first stage is continued during the lag time, i.e., for a period of time that sufficient radiant energy has been absorbed by the culture that synthesis of the biopolymer begins. In the second stage, the artificial illumination of the culture is discontinued and the culture is subjected to diurnal outdoor natural illumination. The second stage is continued to completion of the biopolymer synthesis reaction, i.e., until the desired concentration of biopolymer or desired viscosity level is attained.

The two-stage reaction has the particular advantage of combining a rapid rate of synthesis of the biopolymer with economy of synthesis and is based upon four observations. The first observation is that the lag time preceding the onset of viscosity production in a culture of alga correlates with the rate of absorption of radiant energy in the culture during the early stage of growth, i.e., the higher the rate of absorption the smaller the lag time. The second observation is that the efficiency of biopolymer synthesis correlates with the rate of absorption of the radiant energy during the lag time, the greater the rate of absorption the greater the efficiency. The third observation is that the amount of biopolymer synthesized, i.e., the viscosity level achieved in the culture during a given reaction time, is a function of the cumulative energy absorbed during the reaction time, the higher the cumulative energy absorbed the higher the viscosity level. The fourth observation is that the biopolymer synthesis, and hence viscosity production, once "triggered" or initiated in the first stage continues into a following diurnal cycle of dark/light regimes.

In the two-stage reaction, by employing continuous artificial illumination in the first stage, and with control of the three radiant energy-related parameters, the lag time is decreased. Therefore, to the extent that the lag time is decreased, the time required to obtain a desired amount of biopolymer, or degree of viscosity level, in the culture is decreased and the efficiency of biopolymer synthesis is improved. This further increases the rate of biopolymer synthesis since for any rate of cumulative absorbed radiation a greater amount of biopolymer is synthesized. Additionally, since the amount of biopolymer synthesized is a function of the cumulative radiant energy absorbed, increasing the rate of absorption of the radiant energy increases the rate of biopolymer synthesis. Finally, since the biopolymer synthesis, after having once been "triggered" in the first stage, continues into the second stage employing natural illumination, the economy of employing natural illumination as compared with artificial illumination is combined with the improved rate of synthesis of the biopolymer obtained as a result of carrying out the first stage.

In the synthesis of biopolymer by Porphyridium aerugineum, the first stage of the reaction is carried out employing continuous artificial illumination of such intensity that $\psi_a$ is 0.33 Einstein (0.0165 kw-hr) per day per liter of culture and $(E_a)_c$ is between about 0.66 to 0.89 Einstein (0.033 to 0.045 kw-hr). For the two stages of the reaction, the value of $(E_a)_c$ should be between about 1.2 and 2.0 Einsteins (0.060 to 0.100 kw-hr) per liter and the value of ($\Delta$) should be at least about 0.18 per day to achieve a low shear rate apparent viscosity of the order of 500 centipoises (0.5 pascal-second).

Another aspect of the process for the growth of alga and synthesis of biopolymer involves employing illumination enriched with respect to particular wavelengths, i.e., carrying out the reaction under controlled light quality conditions. By employing illumination of a quality rich in a bandwidth of particular wavelengths, the rate at which the biopolymer is synthesized is greater than the rate of synthesis when full spectrum, i.e., the usual bandwidth of visible light, illumination is employed. Further, efficiency of conversion of the illumination to biopolymer is greater. Additionally, the lag time preceding the synthesis of the biopolymer is shorter. Moreover, the amount of biopolymer synthesized during a given reaction time is greater. In the synthesis of biopolymer by *Porphyridium aerugineum*, these results are achieved employing illumination having its energy content predominantly in the region of 600 to 700 nanometers. By "predominantly" is meant that at least 50% of the energy in the illumination is in the region of 600 to 700 nanometers.

The use of illumination enriched with respect to particular wavelengths may be combined with control of the three radiant energy-related parameters. Further, the illumination employed in the first stage of the two-stage process may be enriched with respect to particular wavelengths.

The following example will illustrate the improved results obtained by synthesizing biopolymer by *Porphyridium aerugineum* employing illumination having its energy content predominantly in the region of 600 to 700 nanometers.

EXAMPLE 4

In this example, *Porphyridium aerugineum* was grown and biopolymer synthesized in a series of cultures containing the components identified hereinabove in Table III, a mixture of 5% carbon dioxide and 95% air being injected continuously into the cultures during the reaction period of 9 days. One group of cultures was provided during the reaction with full spectrum illumination characterized by an incident radiant energy such that the quality of illumination was as follows: in the bandwidth region of 600 to 700 nanometers, the energy content was 0.86 microwatt per $cm^2$ per nanometer; and in the bandwidth region of 400 to 500 nanometers, the energy content was 1.55 microwatts per $cm^2$ per nanometer. The total incident radiation was 4708 ergs (470.8 microjoules) per $cm^2$ per sec. Another group of cultures was provided during the reaction with controlled spectrum illumination characterized by an incident radiant energy such that the quality of illumination was as follows: in the bandwidth region of 600 to 700 nanometers, the energy content was 3.6 microwatts per $cm^2$ per nanometer; and there was negligible energy contribution in the bandwidth of 400 to 500 nanometers. The total incident radiation was 4118 ergs (411.8 microjoules) per $cm^2$ per sec. During the reactions, samples were withdrawn periodically and the low shear rate apparent viscosity measured. In each of the groups of culture, the value of $\psi_a$ was varied, and the lag time, $\theta_b$, measured. The amount of alga grown during the reaction period in each of the cultures was also measured.

Figure 3:
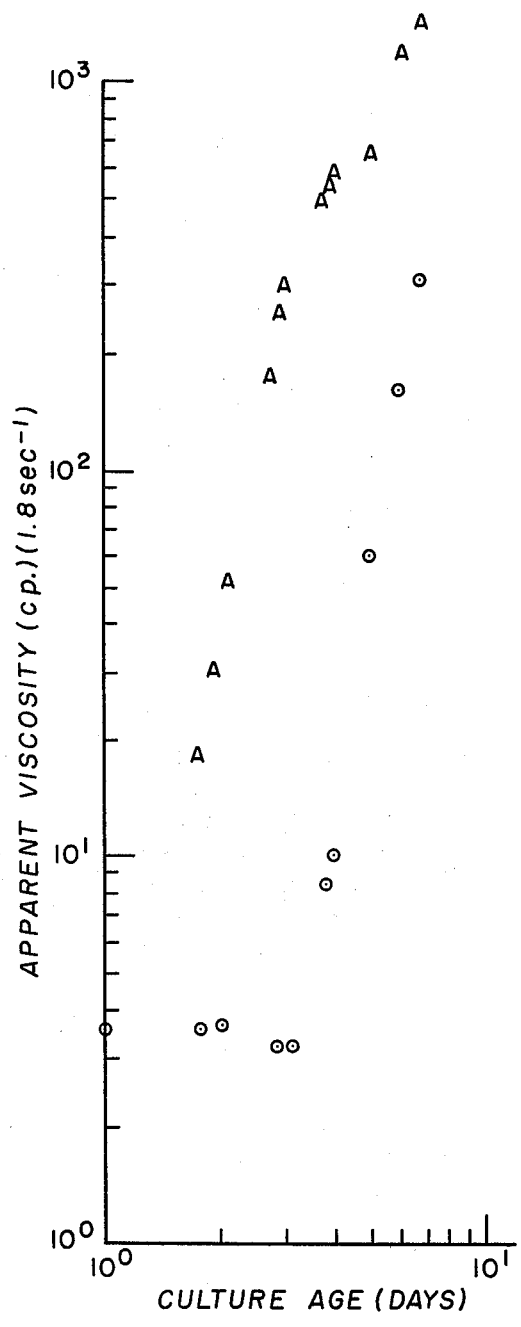
FIG. 3 is a plot of attained apparent viscosity of a culture versus age of the culture under different illumination conditions.
Figure 4:
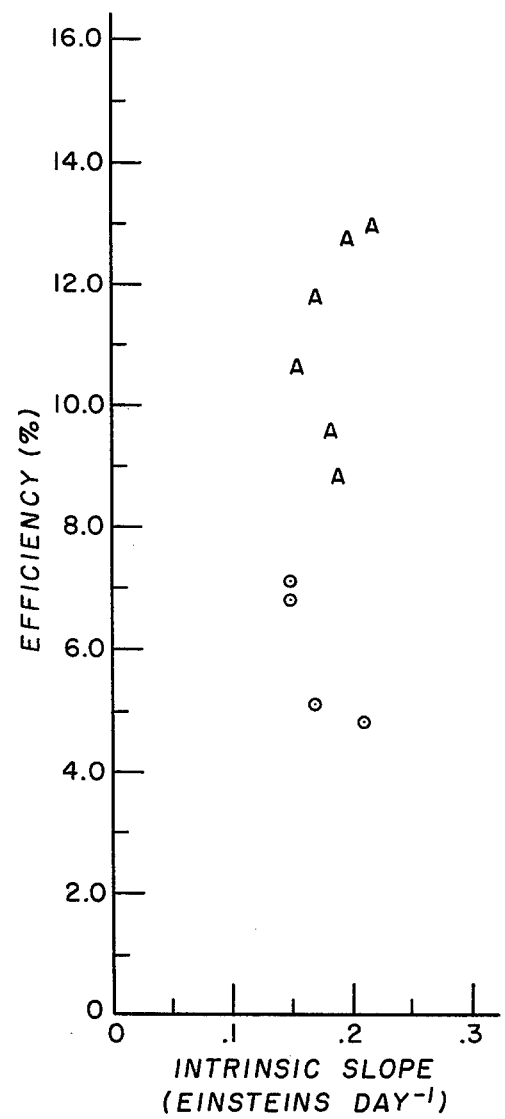
FIG. 4 is a plot of efficiency of biopolymer synthesis versus intrinsic slope of the initial segment of cumulative absorbed radiant energy under different illumination conditions.
Figure 5:
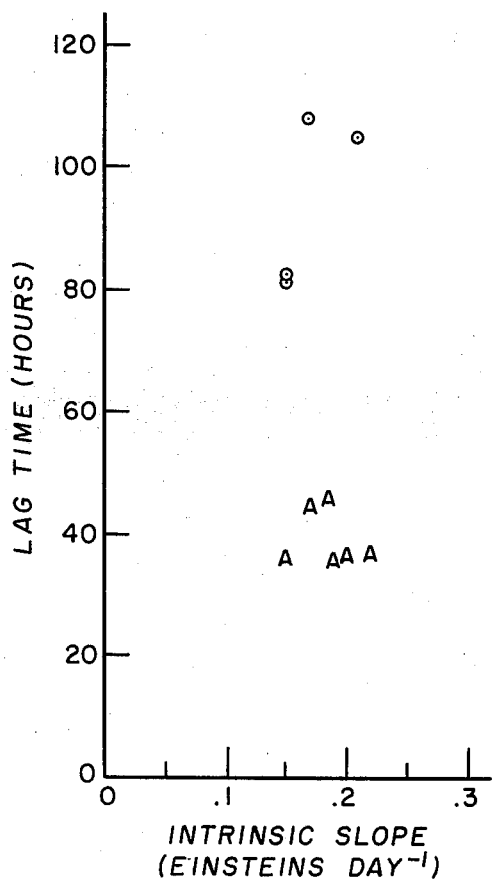
FIG. 5 is a plot of lag time versus intrinsic slope of the initial segment of cumulative absorbed radiant energy under different illumination conditions.
Figure 6:
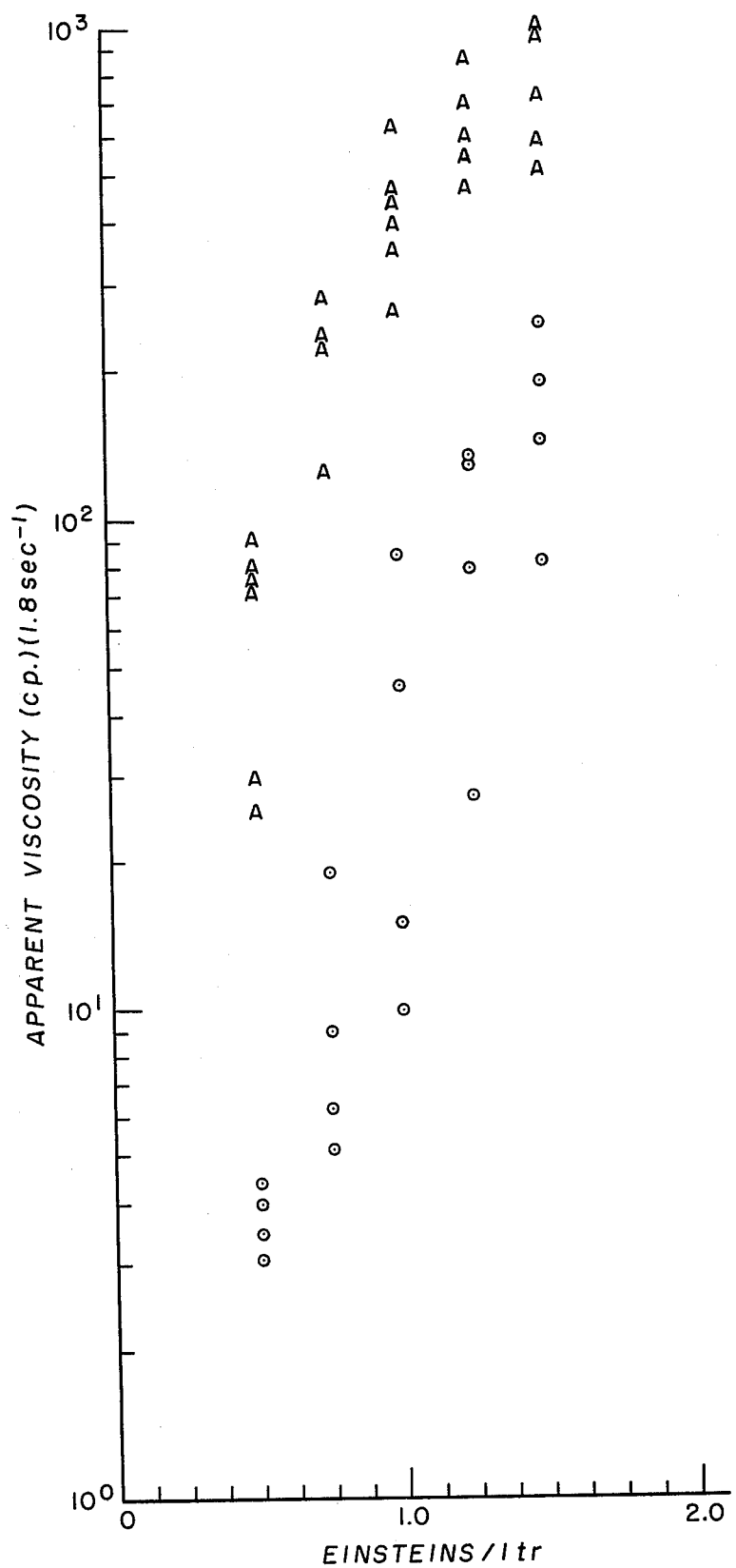
FIG. 6 is a plot of attained apparent viscosity of a culture versus the amount of absorbed radiation under different illumination conditions.

The results are set forth in FIGS. 3 to 6. In FIG. 3 are plotted the low shear rate apparent viscosities of two of the cultures versus the time of reaction, i.e., culture age, one culture being provided with the full spectrum illumination, ☉, and the other being provided with the controlled spectrum illumination, ▲. In FIG. 4 there is shown the efficiency of biopolymer synthesis versus $\psi_a$ for a series of the cultures, one group of the cultures being provided with the full spectrum illumination, ☉, and another group being provided with the controlled spectrum illumination, ▲. In FIG. 5 there is shown the variation in lag time, $\theta_b$, versus $\psi_a$ for two groups of the cultures, one group of the cultures being provided with the full spectrum illumination, O, and the other group being provided with the controlled spectrum illumination, ▲. In FIG. 6 there is shown the amount of biopolymer synthesized as evidenced by the low shear rate apparent viscosity of the culture for various amounts of energy of illumination absorbed for two groups of a series of cultures, one group being provided with the full spectrum illumination, O, and the other being provided with the controlled spectrum illumination, ▲.

It will be observed from FIG. 3 that the low shear rate apparent viscosities of the cultures at comparable ages are greater when employing the controlled spectrum illumination than when employing the full spectrum illumination even though the total incident radiant energy level in the full spectrum illlumination is greater than that in the controlled spectrum illumination.

FIG. 4 shows that the efficiency of conversion of the absorbed radiant energy to biopolymer under comparable conditions of $\psi_a$ is greater with the controlled spectrum illumination than with the full spectrum illumination.

FIG. 5 shows that the lag time under comparable conditions of $\psi_a$ is shorter with controlled spectrum illumination than with full spectrum illumination.

FIG. 6 shows that a higher apparent viscosity level, and hence a greater amount of biopolymer is synthesized for a given amount of absorbed radiant energy, with the controlled spectrum illumination, is obtained than with the full spectrum illumination.

The biopolymers may be "upgraded" with respect to certain characteristics for the purpose of enhancing their use in mobility control. For example, there is a need for improvements in "flow resistance" materials in waterflooding processes which reduce fingering and improve producing characteristics of wells which exhibit rapid water and thickener breakthrough and in so doing aggravate emulsion treating problems in surface equipment. In this aspect of the invention, alga biopolymer is complexed with a heavy metal or transition metal ion, such as trivalent chromium to form a material with improved flow resistance characteristics. Example 5 illustrates the effect of complex formation.

EXAMPLE 5

A series of experiments were performed to compare the flow rate and flow resistance characteristics of solutions of an alga biopolymer before and after the addition of small amounts of trivalent chromium ion as a complexing agent. Here "resistance factor" or RF is defined as the ratio of the flow rate of the biopolymer-free solute to the flow rate of the biopolymer solution, evaluated at the same driving pressure. An aliquot of cell-free supernatant containing in-vivo biopolymer was prepared by centrifuging a suspension withdrawn from a culture of *Porphyridium aerugineum*. The concentrate was diluted to reduce the viscosity and then filtered through an 8-micron (micrometer) millipore filter. The average flow rate was recorded and the low shear rate apparent viscosity measured. A stock solution containing trivalent chromium ion was then injected, with gentle agitation, into the filtered solution to a final concentration of 10 weight parts per million trivalent chromium ion. That the alga biopolymer can be complexed is evident on examination of the results presented in Table IV. In the case of the uncomplexed alga biopolymer, following filtration, the solution viscosity was 13 cp (.013 pascal-second) and the average flow rate through the filter determined to be 2.1 ml per sec. On addition of the chromium ion the complexed alga biopolymer immediately plugged the 8-micron filter. The viscosity was unchanged and there was no evidence of turbidity in the solution.

TABLE IV

| $Cr^{+3}$-wppm | Viscosity-cp* | Appearance | RF | Flow Rate ($cm^3$/sec) |
|---|---|---|---|---|
| 0 | 13 | Clear | 15.2 | 2.1 |
| 10 | 13 | Clear | ∞ | 0 |

*1 centipoise = 0.001 pascal-second

A process for synthesizing biopolymer from alga and its use as a thickening agent in an aqueous driving fluid for the production of petroleum from a petroleum-containing subterranean formation involves synthesis of the biopolymer at the site where the aqueous driving fluid is injected into the subterreanean formation. Any biopolymer-producing alga of the varieties hereinabove described, including the several species of *Porphyridium*, may be employed for synthesizing the biopolymer in this process. The reactors for the synthesis of the biopolymer are located at or in the vicinity of the injection wells. The culture, after the desired viscosity has been obtained, may be directed to a holding tank and then to a separator. In the separator, the biomass, or cells of the alga, is removed from the culture as by centrifugation into a cell-free supernatant containing the in-vivo form of the biopolymer.

In this process, synthesis of the biopolymer, as previously mentioned, may be carried out only to the extent that the viscosity attained by the culture is that desired for the aqueous driving fluid. On the other hand, also as previously mentioned, synthesis may have been carried out to the extent that the viscosity attained by the culture is greater than that desired for the aqueous driving medium. In the latter case, an aqueous phase is added to the culture to bring its viscosity to that desired for the aqueous driving fluid. In either case, the viscous solution for injection into the subterranean formation may have added to it such conditioning agents as flocculants, dispersants, corrosion control agents, fungus and bacteria growth inhibitors, oxygen scavengers, etc. that are conventionally employed in aqueous driving fluids for petroleum recovery.

The biomass or alga cells separated from the culture, again as previously mentioned, may be recycled to the reactors for further synthesis of biopolymer.

As hereinabove noted, the biopolymer may be precipitated from the culture in which it is synthesized. The precipitated biopolymer may then be separated by centrifugation or filtration from the supernatant culture and dried under mild drying conditions for storage, transportation, or otherwise. It may also be suspended in a nonaqueous carrier liquid. The dried biopolymer, also as hereinabove noted, may be used as the thickening agent in the aqueous driving fluid. However, reconstitution of the dried biopolymer by the addition thereto of water results in a loss of thickening ability. In other words, the viscosity of a solution of the reconstituted biopolymer is less than that of an in-vivo solution culture containing the same amount of the biopolymer. Accordingly, the synthesis of the biopolymer on the site at which it is to be employed as the thickening agent for the aqueous driving fluid and its use directly as thickening agent for the aqueous driving fluid avoids the loss of thickening ability encountered with the reconstituted biopolymer.

Example 6 will illustrate the differences in thickener performance between the "in-vivo" and "reconstituted" forms of the biopolymer.

EXAMPLE 6

In this example, the production of biomass and biopolymer by a culture of *Porphyridium aerugineum* was managed under conditions such that the culture attained a low shear rate viscosity on the order of 800 cp (1.8 $sec^{-1}$), corresponding to a biopolymer yield on the order of 1400 weight parts per million. Centrifugation was employed to mechanically separate the biomass from the culture, yielding a viscous supernatant. This supernatant contained a mixture of unadulterated or "in-vivo" biopolymer, other byproducts, and nutrients in various stages of depletion. "Reconstituted" biopolymer was recovered from an aliquot of the supernatant using a procedure which involves addition of an excess of an alcohol and drying under vacuum at moderate temperature conditions. The thickener performance characteristics of both forms of biopolymer are compared in FIGS. 7 and 8. For comparison purposes, there are included data on "Kelzan". In these FIGS. curve 1 is for the in-vivo biopolymer, curve 2 is for the reconstituted biopolymer, and curve 3 is for the Kelzan.

Figure 7:
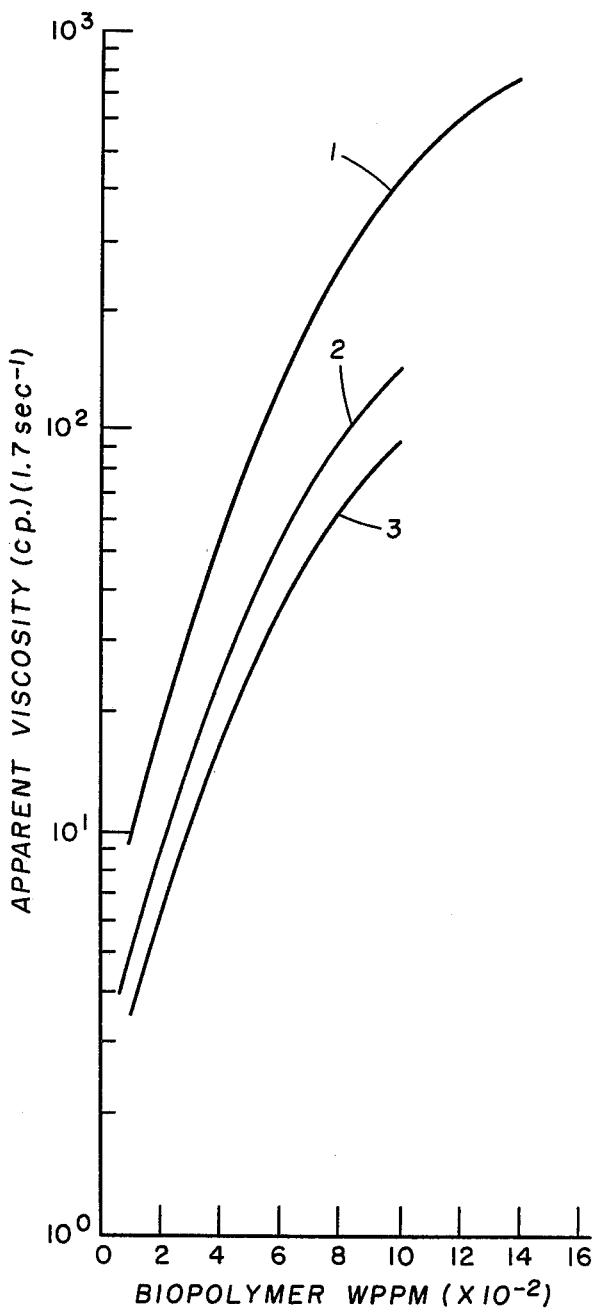
FIG. 7 is a plot of apparent viscosity versus biopolymer concentration for solutions of biopolymers.
Figure 8:
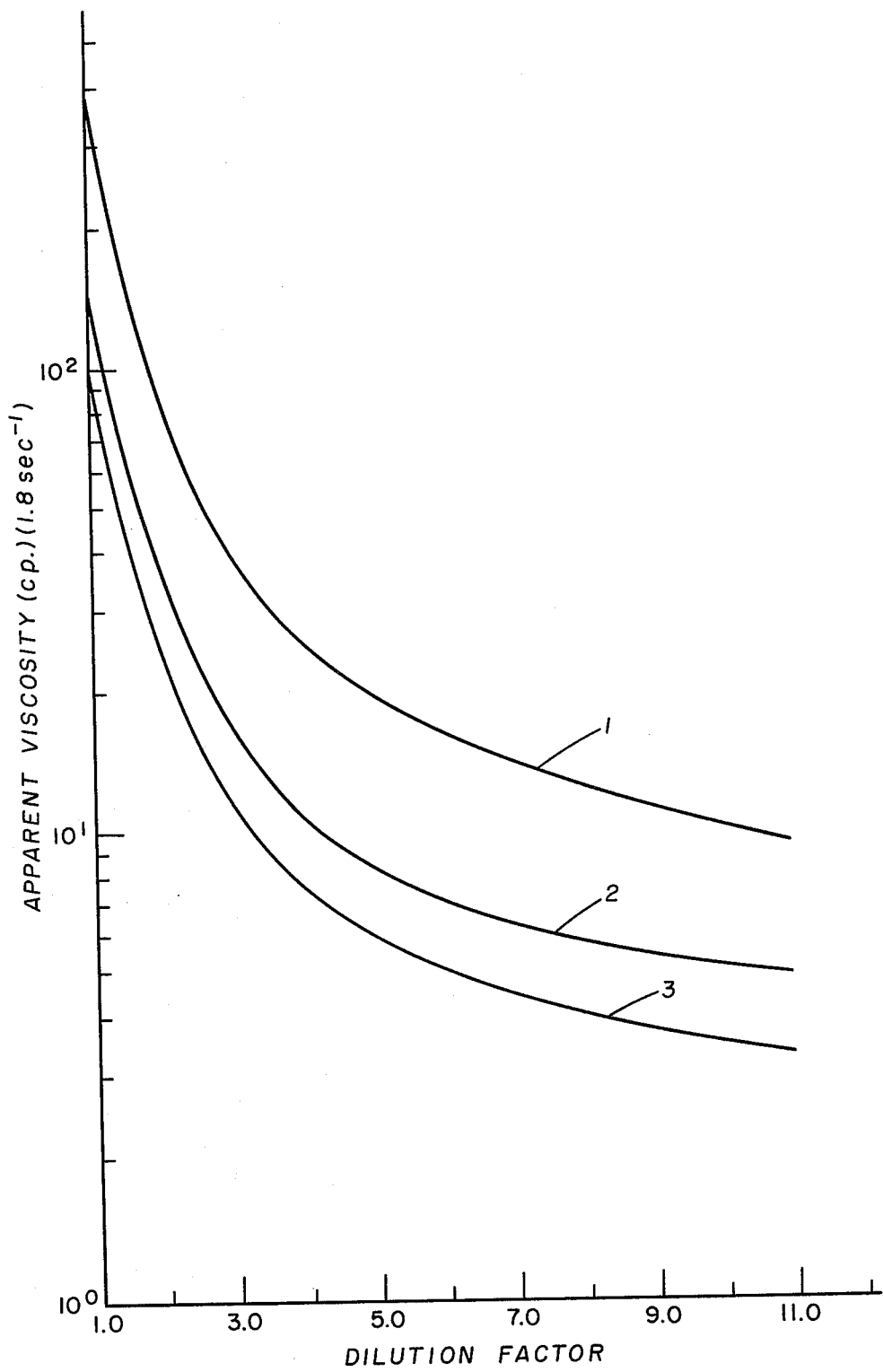
FIG. 8 is a plot of apparent viscosity versus dilution factor for solutions of biopolymers.

FIG. 7 compares the low shear rate viscosity yield per unit weight of biopolymer of "reconstituted" biopolymer, Kelzan, and "in-vivo" biopolymer. The "solvent" is an aqueous solution of 3% NaCl and 0.15% $CaCl_2$. There is shown a twofold to fourfold higher viscosity yield of the "in-vivo" form of the algae biopolymer in the concentration range between 500 wppm to 1000 wppm. The dilution viscosity data given in FIG. 8 show that in the "in-vivo" form the concentrate yields a process viscosity or biopolymer waterflood injection level of 10 cp (0.01 pascal-second) when diluted approximately 1 to 10 vol/vol, i.e., no dilution or initial viscosity level corresponds to a factor of unity. For the same initial concentration, 1 volume of alga biopolymer in solution, "reconstituted" from the concentrate, yields only about 4 volumes of 10 cp (0.01 pascal-second) fluid. The dilution characteristics of "Kelzan" are also compared for the same initial biopolymer concentration.

I claim:

1. In a process for the production of petroleum from a petroleum-containing subterranean formation wherein an aqueous driving fluid containing a thickening agent is injected into said formation through an input well and passed through said formation in the direction of an output well to drive said petroleum in said formation to said output well, the improvement comprising employing as a thickening agent in said aqueous driving fluid an extracellular biopolymer synthesized by an alga.

2. The process of claim 1 wherein said biopolymer is synthesized by an alga selected from the divisions consisting of Rhodophyta, Chlorophyta, Cyanophyta, and Phaeophyta.

3. The process of claim 2 wherein said biopolymer is synthesized by an alga from the division Rhodophyta.

4. The process of claim 3 wherein said biopolymer is synthesized by an alga from the genus Porphyra.

5. The process of claim 4 wherein said biopolymer is synthesized by the alga *Porphyridium aerugineum.*

6. The process of claim 4 wherein said biopolymer is synthesized by the alga *Porphyridium cruentum.*

7. The process of claim 1 wherein said biopolymer is contained in an in-vivo solution.

8. The process of claim 1 wherein said biopolymer has been reconstituted.

9. A process for the synthesis of a biopolymer by an alga comprising growing said alga in a culture containing dissolved therein sodium nitrate in the amount of about 55 to 250 weight parts per million and sodium glycerophosphate in the amount of about 100 to 300 weight parts per million.

10. The process of claim 9 wherein said alga is *Porphyridium aerugineum.*

11. A process for the synthesis of a biopolymer by an alga comprising growing said alga in a culture under illumination and controlling (a) the intrinsic slope of the initial segment of the cumulative absorbed radiant energy versus time curve, (b) the cumulative moles of light quanta absorbed, and (c) the ratio of (a) to (b).

12. The process of claim 11 wherein said alga is *Porphyridium aerugineum.*

13. The process of claim 11 wherein said illumination is enriched with respect to particular wavelengths.

14. The process of claim 11 wherein said culture contains dissolved therein sodium nitrate in the amount of about 55 to 250 weight parts per million and sodium glycerophosphate in the amount of about 100 to 300 weight parts per million.

15. The process of claim 14 wherein said alga is *Porphyridium aerugineum* and said illumination has at least 50% of its energy content in the region of 600 to 700 nanometers.

16. A process for the synthesis of a biopolymer by the alga *Porphyridium aerugineum* comprising growing said alga in a culture under conditions of illumination such that the intrinsic slope of the initial segment of the cumulative absorbed radiant energy versus time curve, (a), is about 0.33 Einstein (0.0165 kw-hr) per liter of culture per day, the cumulative moles of light quanta absorbed, (b), are between 1.2 to 2.0 Einsteins (0.033 to 0.045 kw-hr) per liter of culture, and the value of a/b is about 0.18 per day, the value of (b) during the induction period being between about 0.66 to 0.89 Einstein (0.033 to 0.045 kw-hr) per liter of culture.

17. A process for the synthesis of a biopolymer by an alga comprising growing said alga in a culture in two stages, the culture in the first stage being subjected to artificial illumination and continued for a period of time that sufficient radiant energy has been absorbed that growth of said alga and synthesis of said biopolymer begins and the culture in the second stage being subjected to diurnal natural illumination to continue growth of said alga and synthesis of said biopolymer, said illumination being controlled as to (a) the intrinsic slope of the initial segment of the cumulative absorbed radiant energy versus time curve, (b) the cumulative moles of light quanta absorbed, and (c) the ratio of a to b.

18. The process of claim 17 wherein said alga is *Porphyridium aerugineum.*

19. The process of claim 18 wherein the value of (a) is about 0.33 Einstein (0.0165 kw-hr) per liter of culture per day, the value of (b) during the first and second stages is between about 1.2 to 2.0 Einsteins (0.060 to 0.100 kw-hr) per liter of culture, and the value of a/b is about 0.18 per day, the value of (b) during the first stage being between about 0.66 to 0.89 Einstein (0.033 to 0.045 kw-hr) per liter of culture.

20. The process of claim 19 wherein said culture contains dissolved therein sodium nitrate in the amount of about 55 to 250 weight parts per million and sodium glycerophosphate in the amount of about 100 to 300 weight parts per million.

21. A process for the synthesis of a biopolymer from the alga *Porphyridium aerugineum* comprising growing said alga in a culture under illumination having at least 50% of its energy content in the region of 600 to 700 nanometers.

22. A process for the synthesis of a biopolymer from the alga *Porphyridium aerugineum* comprising growing said alga in a culture containing dissolved therein sodium nitrate in the amount of about 55 to 250 weight parts per million and sodium glycerophosphate in the amount of about 100 to 300 weight parts per million and under conditions of illumination such that the intrinsic slope of the initial segment of the cumulative absorbed radiant energy versus time curve, (a), is about 0.33 Einstein (0.0165 kw-hr) per liter of culture per day, the cumulative moles of light quanta absorbed, (b), are between about 1.2 to 2.0 Einsteins (0.060 to 0.100 kw-hr) per liter of culture, and the value of a/b is about 0.18 per day, said illumination having at least 50% of its energy content in the region of 600 to 700 nanometers.

23. A process for the production of petroleum from a petroleum-containing subterranean formation comprising synthesizing an extracellular biopolymer from an alga, injecting into said formation from an input well an aqueous driving fluid containing as a thickening agent said biopolymer synthesized by said alga to drive said petroleum in said formation in the direction of an output well from which said petroleum can be recovered.

24. The process of claim 23 wherein said biopolymer is *Porphyridium aerugineum.*

25. The process of claim 24 wherein said biopolymer is synthesized by growing said alga in a culture containing dissolved therein sodium nitrate in the amount of about 55 to 250 weight parts per million and sodium glycerophosphate in the amount of about 100 to 300 weight parts per million and under conditions of illumination such that the intrinsic slope of the initial segment of the cumulative absorbed radiant energy versus time curve, (a), is about 0.33 Einstein (0.0165 kw-hr) per liter of culture per day and the cumulative moles of light quanta absorbed, (b), are between about 1.2 to 2.0 Einsteins (0.060 to 0.100 kw-hr) per liter of culture per day, and the value of a/b is at least about 0.18 per day, the illumination having at least 50% of its energy content in the region of 600 to 700 nanometers.

26. The process of claim 25 wherein said biopolymer is synthesized by growing said alga in two stages in a culture containing dissolved therein sodium nitrate in the amount of about 55 to 250 weight parts per million and sodium glycerophosphate in the amount of about 100 to 300 weight parts per million, the culture in the first stage being subjected to artificial illumination for a period of time that sufficient radiant energy has been absorbed that growth of said alga and synthesis of biopolymer begins and the culture in the second stage being subjected to diurnal natural illumination to continue growth of said alga and synthesis of said biopolymer, said illumination being such that the intrinsic slope of the initial segment of the cumulative absorbed radiant energy versus time curve, $(a)$, is about 0.33 Einstein (0.0165 kw-hr) per liter of culture per day, the cumulative moles of light quanta absorbed, $(b)$, are between about 1.2 to 2.0 Einsteins (0.060 to 0.100 kw-hr) per liter of culture, and the value of $a/b$ is about 0.18 per day, said illumination in said first stage having at least 50% of its energy content in the region of 600 to 700 nanometers.

27. The process of claim 26 wherein the value of $(a)$ in said first stage is between about 0.66 to 0.89 Einstein (0.033 to 0.045 kw-hr).

28. The process of claim 23 wherein said biopolymer is synthesized at the site where the aqueous driving fluid containing the biopolymer as thickening agent is injected into the subterranean formation.

29. The process of claim 23 wherein said biopolymer has been complexed with trivalent chromium.

* * * * *